United States Patent
Shepherd et al.

[11] Patent Number: 6,076,904
[45] Date of Patent: Jun. 20, 2000

[54] DISPENSING CABINET

[76] Inventors: Charles G. Shepherd, P.O. Box 64, Oakville, Ontario, Canada, L6J 4Z5; Donald G. Coburn, R.R. #3, Collingwood, Ontario, Canada, L9Y 3Z2

[21] Appl. No.: 09/261,485

[22] Filed: Mar. 3, 1999

[30] Foreign Application Priority Data

Mar. 3, 1998 [CA] Canada .................................. 2230736

[51] Int. Cl.[7] ............................. A47B 81/00; A61B 19/02
[52] U.S. Cl. .......................... 312/209; 312/245; 312/229
[58] Field of Search .................................. 312/206, 207, 312/209, 242, 245, 246, 293.2, 224, 42, 50, 211, 118, 120, 137; 211/88.01, 94.01, 59.2; 206/464, 806; 221/34, 45, 46, 131, 283; D6/512, 515, 524; 232/43.2, 43.5

[56] References Cited

U.S. PATENT DOCUMENTS

| 2,545,089 | 3/1951 | Ladewig | 312/209 |
| 3,151,771 | 10/1964 | Greene | 221/283 X |
| 3,632,180 | 1/1972 | Hauville | 312/209 |
| 4,160,570 | 7/1979 | Bridges | 312/245 |
| 4,767,022 | 8/1988 | Oldorf | 312/42 X |
| 4,775,200 | 10/1988 | Sheu | 312/229 |
| 4,828,121 | 5/1989 | Willcocks, Jr. | 211/94.01 |
| 4,899,886 | 2/1990 | Johansen | D6/515 X |
| 5,022,537 | 6/1991 | Henriquez | 312/245 X |
| 5,785,402 | 7/1998 | DeLorenzo | 312/350 |

FOREIGN PATENT DOCUMENTS

| 1249403 | 11/1960 | France | 312/245 |
| 5228034 | 9/1993 | Japan | 312/247 |

*Primary Examiner*—Peter M. Cuomo
*Assistant Examiner*—James O. Hansen
*Attorney, Agent, or Firm*—Ingrid E. Schmidt

[57] ABSTRACT

A dispensing cabinet has a rear panel, left and right transverse side panels that define a front access opening for the cabinet and a bottom access opening for the cabinet. At least one door is provided to selectively close the front access opening but the bottom access opening remains open. A longitudinally extending rail is mounted on the rear panel and, in a preferred embodiment, extends horizontally to slidably support at least one dispenser in an operative position which is adjacent to the bottom access opening. The dispenser has a bottom opening for dispensing selected articles and these are accessible for use through the bottom access opening. Normally, the door covering the front access opening will be shut and the dispensers are hidden from view. The dispensers are removable from the rail so that selected dispensers may be used according to the nature of the dispensed articles which are required.

16 Claims, 3 Drawing Sheets

6,076,904

1

DISPENSING CABINET

FIELD OF THE INVENTION

This invention relates to a cabinet which may be used for dispensing a variety of disposable articles of the kind which may be used in a dental office such as paper towels, surgical masks, surgical gloves, and drinking cups.

BACKGROUND OF THE INVENTION

Where members of the public, particularly patients, are inevitably exposed to germs and other contaminants, one measure of controlling the spread of disease is to use disposable articles which can be destroyed after use. A disadvantage of using disposable articles is that they tend to be available in dispensing cartons which are likewise disposable and which do not have an attractive appearance, particularly if they are distributed over the surface of a counter. While more permanent dispensers for such articles are available, they must usually be mounted separately and preferably to a wall in order to maximise the available counter space. This is acceptable in some situations, but it is not always desirable or even practical to mount a number of dispensers to a wall. This results in a generally cluttered appearance and also limits the flexibility of the installation in that the dispensers are not usually inter-changeable for dispensing different articles.

An object of this invention is to provide a convenient means of dispensing disposable articles in such a way as to reduce clutter and to provide flexibility.

SUMMARY OF THE INVENTION

In accordance with this invention, there is provided a dispensing cabinet having a rear panel, left and right transverse side panels which define a front access opening for the cabinet and a bottom access opening for the cabinet. At least one door is provided to selectively close the front access opening but the bottom access opening remains open. A longitudinally extending rail is mounted on the rear panel and, in a preferred embodiment, extends horizontally to slidably support at least one dispenser in an operative position which is adjacent to the bottom access opening. The dispenser has a bottom opening for dispensing selected articles and these are accessible for use through the bottom access opening. Normally, the door covering the front access opening will be shut and the dispensers are hidden from view.

In a preferred embodiment of the invention, the front access opening is closed by a pair of hinged doors which have an outer mirrored surface and which allow access to the cabinet for maintaining a supply of articles being dispensed.

The support means for the dispensers on the rail are removable from the rail so that selected dispensers may be used according to the nature of the dispensed articles which are required.

BRIEF DESCRIPTION OF THE DRAWINGS

In order that the invention may be more clearly understood, a preferred embodiment is described below with reference to the accompanying drawings in which.

2

Figure 3:
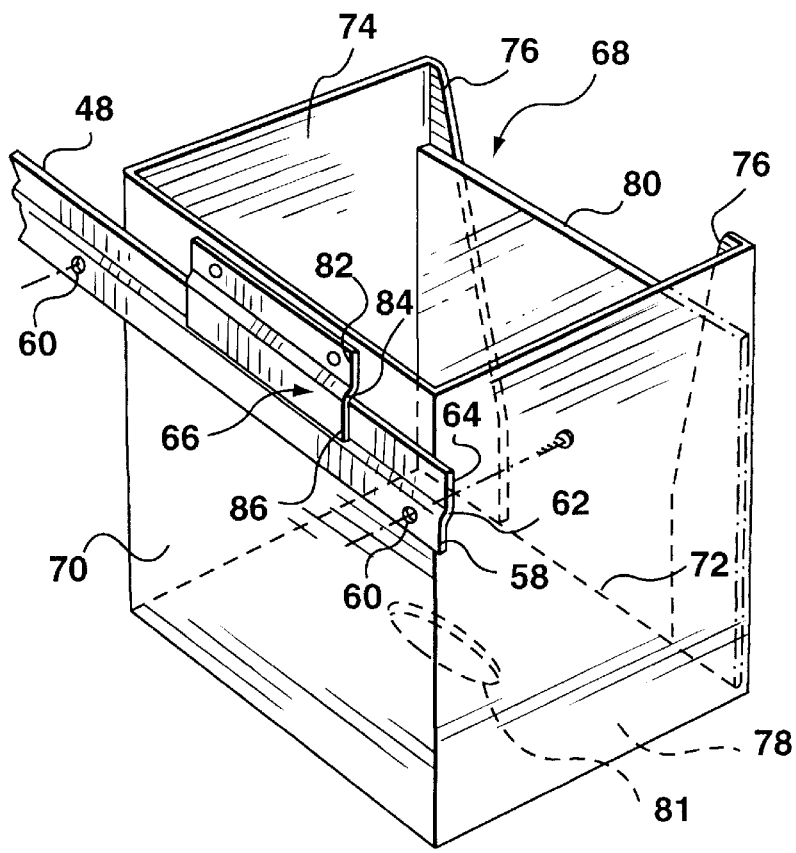
FIG. 3 is a perspective view from the top and rear of a dispenser supported on a rail.
Figure 4:
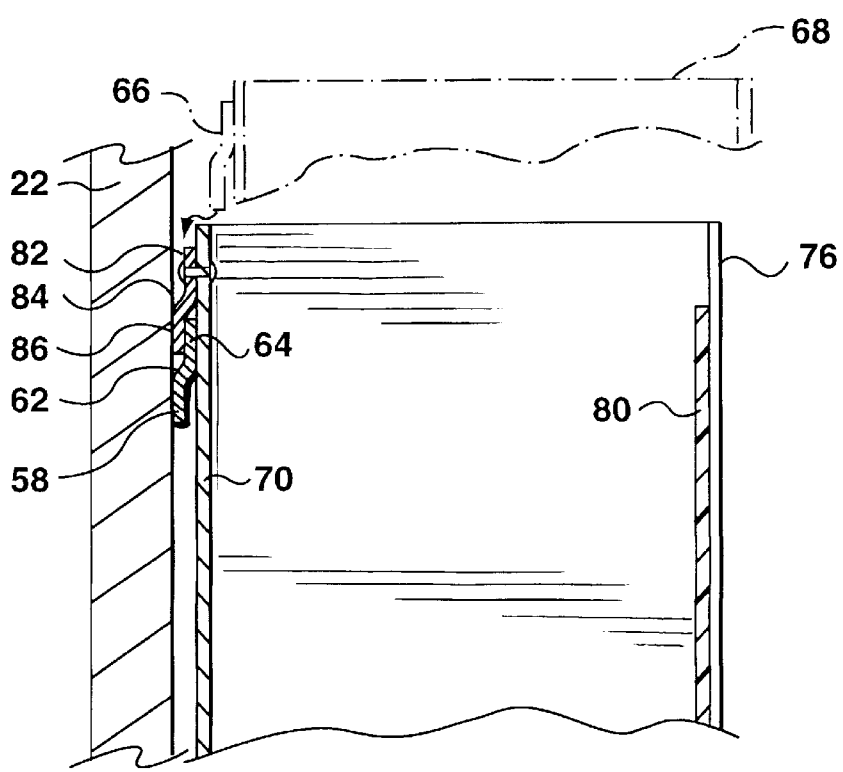
Figure 5:
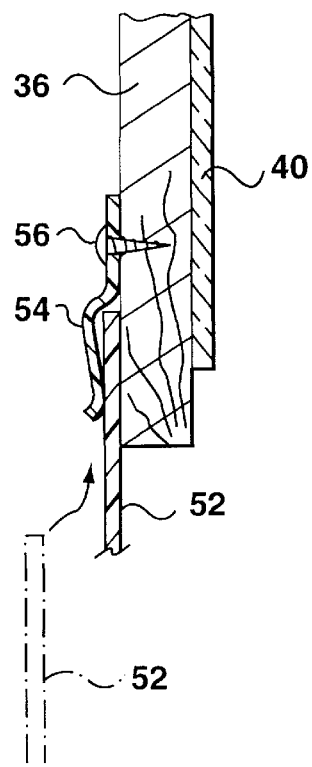
Figure 6:
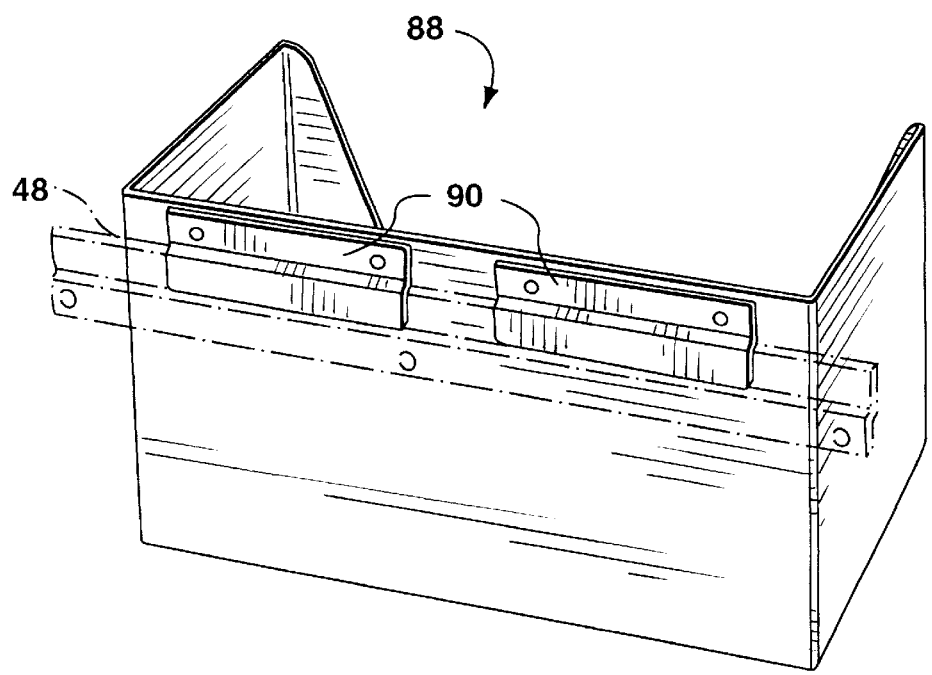

FIG. 4 is a cross-sectional view through a portion of a dispenser supported on a rail in an operative orientation, a portion of the dispenser being shown in broken lines prior to installation on a rail;

FIG. 5 is a cross-sectional view through a portion of a door for the dispensing cabinet; and FIG. 6 is a similar view to FIG. 3 showing a dispenser having a greater length than the dispenser of FIG. 3.

DESCRIPTION OF PREFERRED EMBODIMENT

Figure 1:
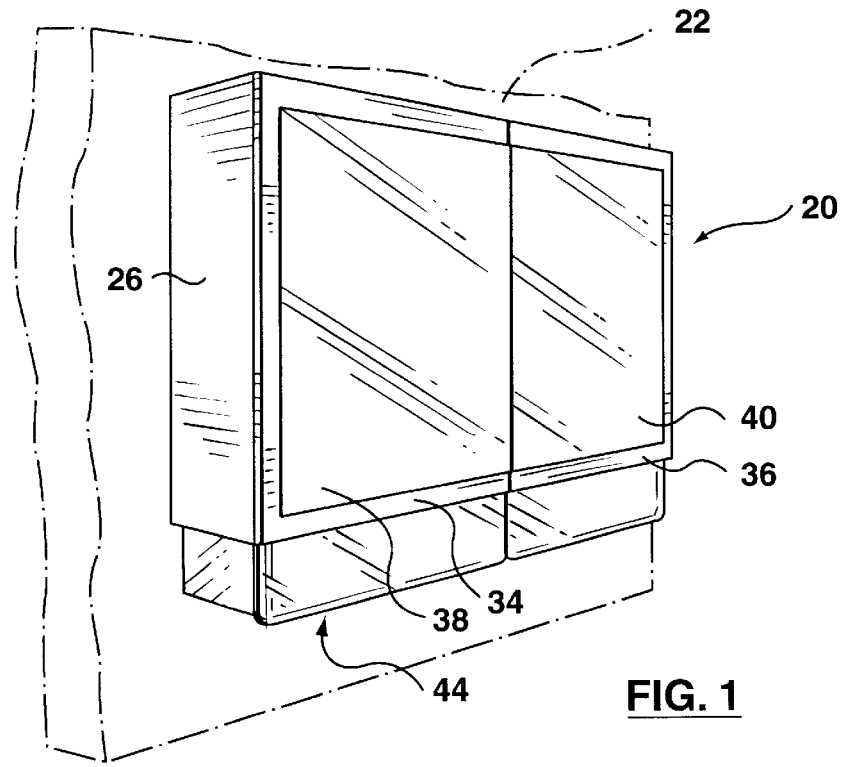
FIG. 1 is a perspective view showing a dispensing cabinet made in accordance with the invention.
Figure 2:
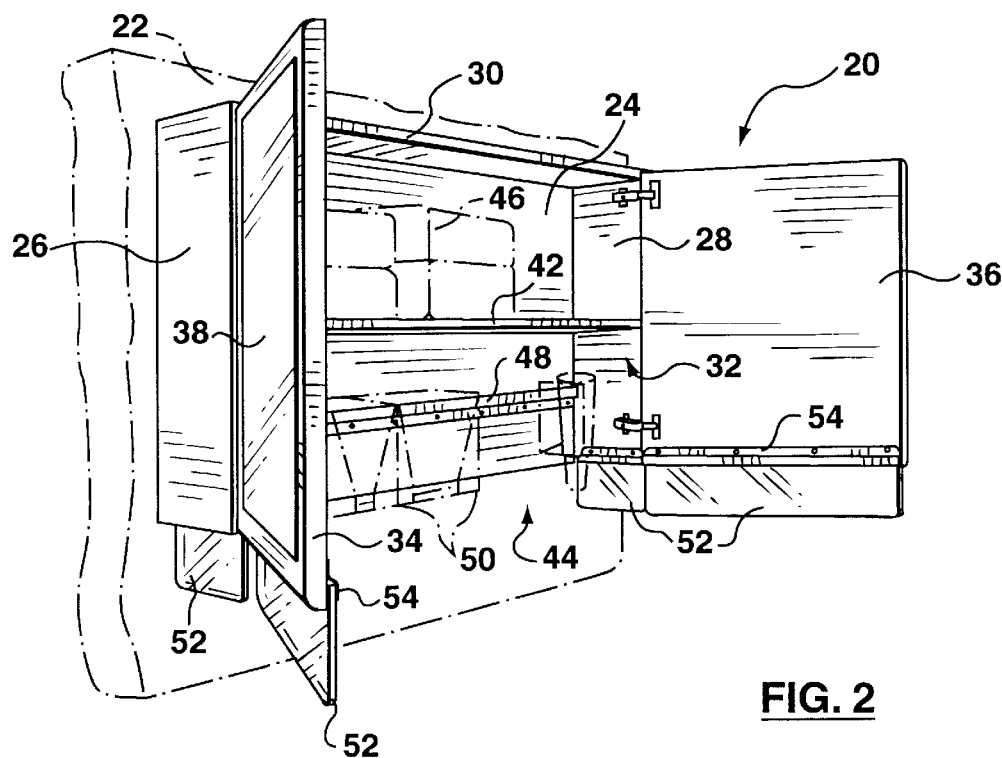
FIG. 2 is a similar view to FIG. 1 with a pair of hinged doors for said cabinet in an open orientation.

A dispensing cabinet made in accordance with the invention is indicated in FIG. 1 by reference numeral 20. The cabinet 20 is mounted to a wall 22 and comprises a rear panel 24 (FIG. 2), a left transverse side panel 26 and a right transverse side panel 28. A top panel 30 is orthogonal to both the side panels 26, 28 and the rear panel 24 and closes the cabinet 20 at a top end thereof, in conventional fashion. A front access opening generally indicated by reference numeral 32 is defined between the left and right side panels 26, 28 and extends from the top panel 30 to the bottom of the left and right side panels 26, 28. The front access opening is closed by a pair of doors 34, 36 hinged to a respective side panel 26, 28. The front outer surface of the doors 34, 36 is conveniently covered with respective mirror tiles 38, 40. The interior of the cabinet further includes a horizontally-disposed storage shelf 42 which is upwardly spaced from a bottom access opening generally indicated by reference numeral 44 and defined by the left and right side panels 26, 28. Various supplies 46 are supported on the storage shelf 42.

A longitudinally-extending rail 48 is mounted horizontally on the rear panel 24 at a height intermediate to the bottom access opening 44 and the storage shelf 42, the height being commensurate with the height of dispensers 50 supported on the rail. The dispensers 50 are characterized by having respective bottom openings through which selected articles may be dispensed. Such articles may comprise paper towels, surgical masks, surgical gloves, or disposable cups and are accessible for use through bottom access opening 44 even while the doors 34, 36 are closed in the orientation shown in FIG. 1. When the supply of articles dwindles, the doors 34, 36 may be opened and the dispensers 50 may be replenished with supplies 46.

It will be understood that the articles being dispensed from the dispensers 50 may project through the bottom opening 44. The cabinet is therefore provided with a number of translucent shields 52 which extend downwardly from the side panels 26, 28 and the doors 34, 36. The articles being dispensed may be seen through the shields 52 and these also define a physical barrier to any aerosols in the surrounding atmosphere which could contaminate the articles prior to use.

One manner of fixing the translucent shields 52 to the cabinet panels and doors is illustrated in FIG. 5. Here, the right side door 36 supports a longitudinally-extending rail 54 which extends throughout the width of the door 36, the rail being fixed to the rear surface of the door by means of suitable fasteners 56. The rail 54 has a curved outwardly-extending portion which is inherently biased for engagement with the inner surface of the door 36 and which can be flexed outwardly to admit an upper edge of a shield 52.

Conveniently, the dispensers 50 are removably supported on the rail 48 so that selected dispensers may be used in accordance with the nature of the dispensed articles which are required. The rail 48 for supporting the dispensers is more clearly shown in FIG. 3 and comprises a first planar portion 58 which would be mounted horizontally to the rear panel 24 with suitable fasteners received through mounting openings 60. A transverse portion 62 extends outwardly from the rear panel 24 in use and a second planar portion 64 extends upwardly from the transverse portion 62. The second planar portion 64 is therefore spaced from the supporting rear panel 24 so as to define a horizontally-extending slot that slidably receives support means 66 for the associated dispenser 68.

The dispenser 68 has a back portion 70, side walls 72, 74 orthogonal to the back portion and a front portion which is only partially closed by left and right spaced front portions 76 which converge towards the bottom 78 of the dispenser. Optionally, as indicated in FIG. 3, a translucent panel 80 may be placed behind the front portions 76 to obstruct a front opening defined between the front portions 76 while permitting the user to visually inspect the dispenser 68 and assess whether supplies need to be supplemented. It will be seen that the top of the dispenser is open and that the bottom 78 has an opening 81 which is shaped suitably for discharging the articles to be contained by the dispenser.

The support means 66 may be formed integrally with the back portion 70. In the embodiment shown, a separate rail portion is fixed to the back portion 70 and comprises a first planar portion 82 mounted to a back portion of the dispenser 68, a transverse portion 84 extending outwardly from the back portion and a second planar portion 86 which extends downwardly from the transverse portion and which is spaced from the back portion 70 of the dispenser 68 to define therebetween a slot for slidably receiving the upwardly-extending planar portion 64 on the support rail 48. In this way, the dispenser 68 can be selectively positioned on the rail 48 at any desired location along the length thereof. A variety of such dispensers may be mounted to the rail and exchanged or substituted, as warranted. This provides the user with appreciable flexibility while affording convenience. An alternative dispenser indicated by numeral 88 in FIG. 6 is included to show that the support means may comprise two rail portions 90, each mounted to a back portion of the dispenser where the dispenser has a greater width.

It will be understood that several variations may be made to the above-described embodiment of the invention as will be apparent to those skilled in the art and which will be within the scope of the appended claims. In particular, it will be noted that the nature of the cabinet and its configuration may vary considerably, that the mirror tiles are optional and that the manner of supporting the dispensers so that they are operatively positioned for dispensing articles through a bottom access opening may also be varied.

We claim:

1. A dispensing cabinet having a rear panel, and left and right transverse side panels defining a front access opening for the cabinet and a bottom access opening for the cabinet, and at least one door adapted to selectively close the front access opening, a longitudinally-extending rail mounted on said rear panel and adapted to support at least one dispenser in an operative position adjacent said bottom access opening;

at least one dispenser having support means for supporting the dispenser on said rail, the dispenser being adapted to dispense selected articles through a bottom opening thereof, said articles being accessible for use through said bottom access opening with said at least one door in a closed orientation closing the front access opening, the front access opening providing access to said at least one dispenser for maintaining a supply of articles being dispensed; and at least one translucent shield mounted on said at least one door and extending below said at least one door, said translucent shield providing visual access to articles extending downwardly from said dispensers and defining a barrier to aerosols.

2. Dispensing cabinet according to claim 1 having a top panel transverse to said rear panel and to said side panels.

3. Dispensing cabinet according to claim 1 having two doors hinged to respective side panels.

4. Dispensing cabinet according to claim 1 having a horizontally-disposed storage shelf upwardly spaced from said bottom access opening.

5. A dispensing cabinet having a rear panel, and left and right transverse side panels defining a front access opening for the cabinet and a bottom access opening for the cabinet, and at least one door adapted to selectively close the front access opening, a longitudinally-extending rail mounted on said rear panel and adapted to support at least one dispenser in an operative position adjacent said bottom access opening, the rail comprising a first planar portion mounted horizontally to said rear panel, a transverse portion extending outwardly from said rear panel, and a second planar portion extending upwardly from the transverse portion and spaced from the rear panel, the second planar portion and the rear panel defining therebetween a horizontally-extending slot for slidably receiving support means for said at least one dispenser;

at least one dispenser having support means for removably supporting the dispenser on said rail, the support means comprising a first planar portion mounted to a back portion of said at least one dispenser, a transverse portion extending outwardly from said back portion, and a second planar portion extending downwardly from said transverse portion and spaced from said back portion, the second planar portion and said back portion defining therebetween a slot for slidably receiving the upwardly-extending second planar portion on said rail, so that said at least one dispenser may be selectively positioned on said rail at a selected longitudinal position;

the dispenser being adapted to dispense selected articles through a bottom opening thereof, said articles being accessible for use through said bottom access opening with said at least one door in a closed orientation closing the front access opening, the front access opening providing access to said at least one dispenser for maintaining a supply of articles being dispensed.

6. Dispensing cabinet according to claim 5 having a top panel transverse to said rear panel and to said side panels.

7. Dispensing cabinet according to claim 5 having two doors hinged to respective side panels.

8. Dispensing cabinet according to claim 5 having a horizontally-disposed storage shelf upwardly spaced from said bottom access opening.

9. A dispensing cabinet having a rear panel, and left and right transverse side panels defining a front access opening for the cabinet and a bottom access opening for the cabinet, and at least one door adapted to selectively close the front access opening, mounting means mounted on said rear panel for supporting at least one dispenser in an operative position adjacent said bottom access opening;

at least one dispenser having support means for supporting the dispenser on said mounting means, the dispenser being adapted to dispense selected articles through a bottom opening thereof, said articles being accessible for use through said bottom access opening with said at least one door in a closed orientation closing the front access opening, the front access opening providing access to said at least one dispenser for maintaining a supply of articles being dispensed; and at least one translucent shield mounted on said at least one door and extending below said at least one door, said translucent shield providing visual access to articles extending downwardly from said dispensers and defining a barrier to aerosols.

10. Dispensing cabinet according to claim 9 having a top panel transverse to said rear panel and to said side panels.

11. Dispensing cabinet according to claim 9 having two doors hinged to respective side panels.

12. Dispensing cabinet according to claim 9 having a horizontally-disposed storage shelf upwardly spaced from said bottom access opening.

13. A dispensing cabinet having a rear panel, and left and right transverse side panels defining a front access opening for the cabinet and a bottom access opening for the cabinet, and at least one door adapted to selectively close the front access opening, the bottom access opening defining an area bounded by peripheral edges of the left and right side panels, said rear panel and said at least one door, mounting means mounted on said rear panel for supporting at least one dispenser adjacent said bottom access opening; and at least one dispenser having support means for supporting the dispenser on said mounting means, the dispenser having at least one side panel which is at least partially closed and a bottom, the bottom having a bottom opening through which articles may be dispensed with said at least one door in a closed orientation fully closing the front access opening to the cabinet, the front access opening providing access to said at least one dispenser for maintaining a supply of articles being dispensed, and said articles being accessible for use through said bottom access opening with said at least one door in a closed orientation closing the front access opening.

14. Dispensing cabinet according to claim 13 having a top panel transverse to said rear panel and to said side panels.

15. Dispensing cabinet according to claim 13 having two doors hinged to respective side panels.

16. Dispensing cabinet according to claim 13 having a horizontally-disposed storage shelf upwardly spaced above said bottom access opening.

* * * * *